United States Patent [19]

Lankford et al.

[11] Patent Number: 5,558,668
[45] Date of Patent: Sep. 24, 1996

[54] MEDICAL LASER TREATMENT SYSTEM AND METHOD

[75] Inventors: Donald M. Lankford, Acton, Mass.; Thomas S. MacGregor, III, Mantua, N.J.; Charles C. Negus, Taunton, Mass.

[73] Assignee: PLC Medical Systems, Inc., Milford, Mass.

[21] Appl. No.: 320,946

[22] Filed: Oct. 11, 1994

[51] Int. Cl.$^6$ .................................................. A61B 17/36
[52] U.S. Cl. .................................... 606/14; 606/19; 606/13
[58] Field of Search ......................... 606/2, 3, 7, 10–17, 606/19

[56] References Cited

U.S. PATENT DOCUMENTS

| | | | |
|---|---|---|---|
| 4,638,800 | 1/1987 | Michel | 606/14 |
| 4,911,712 | 3/1990 | Harrington | 606/14 |
| 4,917,083 | 4/1990 | Harrington et al. | 606/15 |
| 4,971,034 | 11/1990 | Doi et al. | 606/15 |
| 5,030,217 | 7/1991 | Harrington | 606/14 |

OTHER PUBLICATIONS

Reich et al, "$CO_2$ Lasers . . . Losses" *Obstetrics and Gynecology*, vol. 77, No. 1, 1991, pp. 40–47.

*Primary Examiner*—Angela D. Sykes
*Assistant Examiner*—Michael Peffley
*Attorney, Agent, or Firm*—Iandiorio & Teska

[57] ABSTRACT

An improved medical laser treatment system and method generates a beam of laser energy at a predetermined wavelength; transmits the beam of laser energy along a path to a medical treatment site; delivers to the medical treatment site an insufflating gas which is absorbent at the predetermined wavelength; and introduces into the path of the beam of laser energy a non-absorbent purge gas which is transparent to the predetermined wavelength of the laser, at a flow rate for opposing the influx of insufflating gas to reduce the resonant absorption of the laser beam energy.

14 Claims, 4 Drawing Sheets

MEDICAL LASER TREATMENT SYSTEM AND METHOD

FIELD OF INVENTION

This invention relates to an improved medical laser treatment system and method, and more particularly to such a system and method which sharply reduces attenuation and diffusion of the laser beam energy caused by an insufflating or other gas.

BACKGROUND OF INVENTION

The surgical technique of endoscopy allows a surgeon to perform diagnostic or surgical procedures in a minimally invasive manner. Laparoscopy requires inflating or insufflating the patient's abdominal cavity with gas. Distension of the abdomen by the insufflating gas allows the surgeon to visualize the organs and other internal structures by use of a laparoscopic telescope (laparoscope). The laparoscope is generally placed through an incision made in the umbilicus. Surgical instruments may be introduced either though a tureen in an operating laparoscope or through additional punctures in the abdominal wall.

The pressures necessary to adequately distend the abdomen are typically in the 12–14 mm Hg (0.25 psi) range. One of the concerns in this type of surgical procedure is the possibility of forcing some of the insufflating gas into an open blood vessel. Gas bubbles in the bloodstream may pose a risk of embolism. The use of various gases has been explored and the preferred gas for insufflating the patient is carbon dioxide ($CO_2$). $CO_2$ gas is preferred due to its rapid absorption in blood. This minimizes the potential for embolism.

One of the instruments commonly used through, or in conjunction with the laparoscope is the $CO_2$ laser. This type of laser uses a $CO_2$ molecule to generate an output wavelength of 10.6 μ. While this type of laser is very efficient in most applications for which it is intended, its efficacy ill endoscopy is adversely affected by the $CO_2$ gas environment at the surgical site. Since the 10.6 micron wavelength of this laser is emitted by the $CO_2$ molecule this molecule may also absorb photons of this wavelength. This phenomenon is called resonant absorption. When this occurs in the confines of the laparoscope lumen two things happen. First, the absorption of the 10.6 μ laser energy by the $CO_2$ gas results in a loss of laser power transmitted to the target tissue. Second, the uneven heating of the $CO_2$ gas in the laparoscope lumen results in creation of a gas lens within the lumen. This lensing causes distortion of the laser energy that does reach the tissue. This secondary gas lensing effect has an often dramatic effect in reducing the efficacy of the $CO_2$ laser.

Another endoscopic procedure, arthroscopy, allows the surgeon to view or perform surgery on the internal structres of the joints through an arthroscopic telescope (arthroscope). Distension of the joint allows visualization of the internal structures. Though liquids are often used to distend the joint gas is used whenever a $CO_2$ laser is to be employed. $CO_2$ gas is generally preferred for this purpose. Again, the $CO_2$ gas used to distend the joint can adversely affect the transmitted $CO_2$ laser beam. One approach to this problem is to shift the output wavelength of the $CO_2$ laser out of the absorption range of the $CO_2$ insufflating gas. This wavelength shift is accomplished by changing the isotope of $CO_2$ gas used in the laser gas mixture. See U.S. Pat. No. 5,062,842. One isotope used to generate the standard 10.6 μ wavelength is the $C^{12}$ isotope. This is the most common isotope of $CO_2$ gas and the same isotope that is used for insufflating the patient. For the 11.1 μ wavelength output, the less common $C^{13}$ isotope of $CO_2$ is used.

The possibility of using one of the other isotopes of $CO_2$ gas as the insufflating medium was abandoned due to the extremely high cost of these gases. Due to the amount of $CO_2$ gas consumed during the average procedure the cost per procedure would be prohibitive.

Another approach that has been taken is to increase the flow of $CO_2$ gas through the lumen of the endoscope. As the rate of flow of the $CO_2$ gas through the lumen is increased, the effect of the lensing is reduced. While the problem of loss of laser energy through absorption in the gas remains, the effects of the lensing are somewhat mitigated.

While research into the use of other gases for laparoscopic insufflation found that some institutions do use nitrous oxide ($N_2O$) gas, general resistance to this gas was high. In fact many anesthesiologists interviewed felt that use of any gas other than $CO_2$ was too risky. While $N_2O$ is more rapidly absorbed than many other gases, it is itself an anesthetic. Absorption of the gas within the cavity could unnecessarily complicate anesthesia during long procedures. $N_2O$ also supports combustion much as oxygen does. This can increase the likelihood of a fire should a heat source (laser) contact a flammable material in the operating theater.

SUMMARY OF INVENTION

It is therefore an object of this invention to provide an improved medical laser treatment system and method.

It is a further object of this invention to provide such an improved medical laser treatment system and method which has increased power density at the treatment site.

It is a further object of this invention to provide such an improved medical laser treatment system and method which has increased power transmission and sharper laser beam focus at the treatment site.

It is a further object of this invention to provide such an improved medical laser treatment system and method which is more reliable, quicker and more efficient.

The invention results from the realization that an improved, more efficient medical laser treatment system and method can be effected by introducing into the laser beam path a trickle flow of purge gas which is transparent or non-absorbing at the laser beam wavelength to oppose the entry into the laser beam path of an absorbing gas such as an insufflating gas which is absorbent at the laser beam wavelength in order to reduce resonant absorption of the laser beam energy and thereby provide increased energy at the medical treatment site.

This invention features an improved medical treatment laser system including a gas laser for generating a beam of laser energy at a predetermined wavelength, means for transmitting the beam of laser energy to the medical treatment site, and means for delivering to the medical treatment site an insufflating gas which is absorbent at the predetermined wavelength. The improvement includes means for introducing, to the means for delivering the laser beam, a non-absorbent purge gas which is transparent to the predetermined wavelength of the gas laser at a flow rate for opposing the influx of insufflating gas to the means for delivering and reducing resonant absorption of the laser beam.

In a preferred embodiment the insufflating gas may be carbon dioxide, the gas laser may be a carbon dioxide laser, the purge gas may be inert, and it may be argon. The means for transmitting may include a laparoscope. The means for delivering may include a cannula associated with the laparoscope. The means for introducing may include support means on the laparoscope for receiving the purge gas. The purge gas may be introduced at a flow rate of approximately 0.1–0.5 liters per minute.

The invention also features an improved medical laser treatment method including the steps of generating a beam of laser energy at a predetermined wavelength; transmitting the beam of laser energy along a path to the medical treatment site, delivering to the medical treatment site an insufflating gas which is absorbent at the predetermined wavelength and introducing into the path of the beam of laser energy a non-absorbent purge gas which is transparent to the predetermined wavelength of the laser at a flow rate for opposing the influx of insufflating gas to reduce the resonant absorption of laser beam energy. In a preferred embodiment the insufflating gas may include carbon dioxide. The purge gas may be inert and it may be argon. The purge gas may be introduced at approximately 0.1–14 0.5 liters per minute.

DISCLOSURE OF PREFERRED EMBODIMENT

Other objects, features and advantages will occur to those skilled in the art from the following description of a preferred embodiment and the accompanying drawings, in which.

This invention may be accomplished with an improved medical laser treatment method which includes generating a beam of laser energy at a predetermined wavelength such as 10.6 µ for example using a $CO_2$ surgical laser which produces a 10.6 µ wavelength laser beam. The beam of laser energy is transmitted along a path to a medical treatment site. Typically the path is an articulated optical delivery arm which can be manipulated by the surgeon. The medical treatment site is on or in a human patient. In some cases, in order to perform surgery, the treatment site must be inflated or insufflated in order to make room the surgeon to see and manipulate the surgical instruments and laser beam. In such cases an insufflating gas is delivered to the medical treatment site. This insufflating gas is typically $CO_2$ which is normally desired because it has the least possibility of being lethal to the patient. However, $CO_2$ gas is an excellent resonant absorbent of the 10.6 µ wavelength laser beam energy generated by the $CO_2$ laser. In order to remove the insufflating $CO_2$ gas from the laser beam path, a purge gas according to this invention is introduced into the path of the beam of laser energy. The purge gas is a non-absorbent gas which is transparent to the predetermined wavelength of the laser and is introduced at a flow rate such that the insufflating $CO_2$ gas is cleared or virtually cleared from the laser beam path. This reduces the resonant absorption of the laser beam energy. The result is a laser beam which loses less energy and is less apt to be diffused by the $CO_2$. The purge gas may be any type of inert gas which is non-absorbing or transparent at the laser energy wavelength. Some gases which are preferred for purge gas are argon and nitrous oxide. The flow required of the purge gas is usually 0.1–0.5 liters per minute. This is normally sufficient to overcome the pressure of the insufflating $CO_2$ gas at the medical treatment site inside the patient's body. But this can vary. Obese people will require higher pressure to inflate the abdominal cavity, for example, in which case the purge gas may be required to be introduced at a higher pressure to achieve the standard flow of 0.1 to 0.5 lpm. The pressure of the insufflating gas is typically 12–14 mm of mercury or about 0.25 pound per square inch, and the flow rate can be anywhere from 0 to 5 liters per minute, depending upon the patient and the cavity and other ambient conditions. Although in the specific embodiment disclosed hereinafter, the delivery system terminates with a laparoscope, this is not a necessary limitation as any desired device could be used there such as an arthroscope, thoroscope, endoscope or pelviscope. The insufflating gas may be delivered into the body cavity through a cannula associated with or surrounding a laparoscope. The purge gas may be introduced through a port in the laparoscope or other scope that is used.

Figure 1:
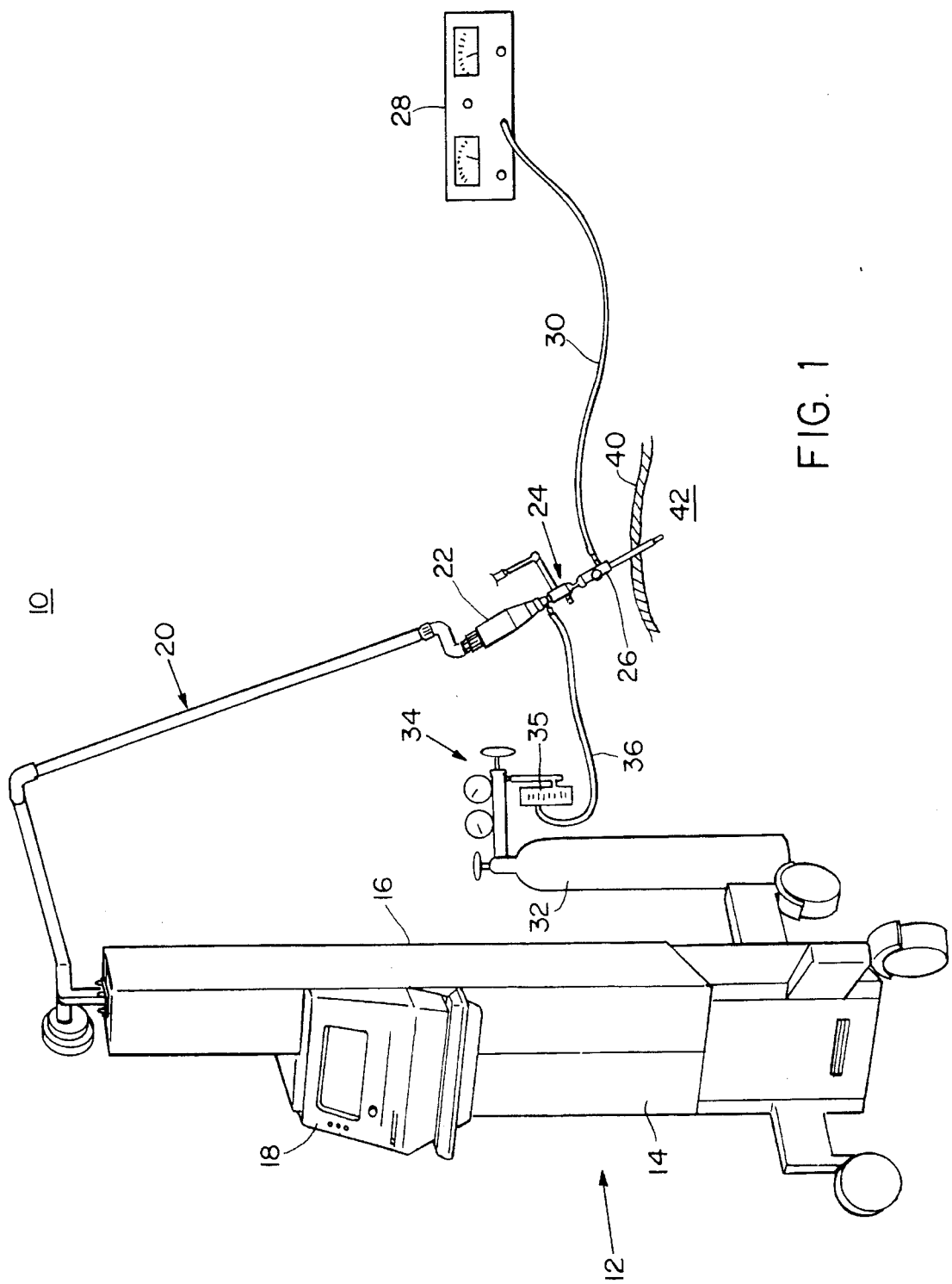
FIG. 1 is a three-dimensional diagrammatic view of an improved medical laser treatment system according to this invention.

There is shown in FIG. 1 an improved medical laser treatment system 10 which includes a conventional surgical laser 12 including a power supply 14, $CO_2$ laser 16, control panel 18, and an articulated arm delivery system 20 which terminates in a $CO_2$ laser coupler 22 and endoscope 24 associated with a cannula 26. The $CO_2$ is provided to cannula 26 by $CO_2$ insufflator 28 through hose 30. Argon purge gas is supplied to laparoscope 24 from pressurized tank 32 through two-stage regulator 34, flow meter 35, and hose 36. Laparoscope 24 and cannula 26 are shown inserted through the abdomen wall 40 into the abdominal cavity 42 of a living patient. $CO_2$ insufflating gas is typically fed through hose 30 at a rate of 0–5 liters per minute and is delivered through one-way stopcock 44, FIG. 2, to cannula 26. Cannula 26 is sealed at its upper end 46 to the body of laparoscope 24 so that the carbon dioxide 45, indicated by the curly lines, exits in the annular channel 47 between cannula 26 and laparoscope 24. Actuator button 48 permits the surgeon to close a flapper valve at the upper end 46 of cannula 26 as laparoscope 24 is withdrawn so that the patient's abdominal cavity remains sealed by the in-place cannula 26 even after laparoscope 24 is withdrawn and while awaiting a new laparoscope or other instrument to be inserted. The laparoscope 24, laser coupler 22, articulated arm delivery system 20, and cannula 26, are all of well-known construction and are conventionally available standard items. The argon or other purge gas delivered in hose 36 enters laparoscope 24 through one-way petcock 50. This purge gas passes through the operating channel of the laparoscope and exits the laparoscope at its distal end 52 as indicated by the curly lines 54.

Figure 3:
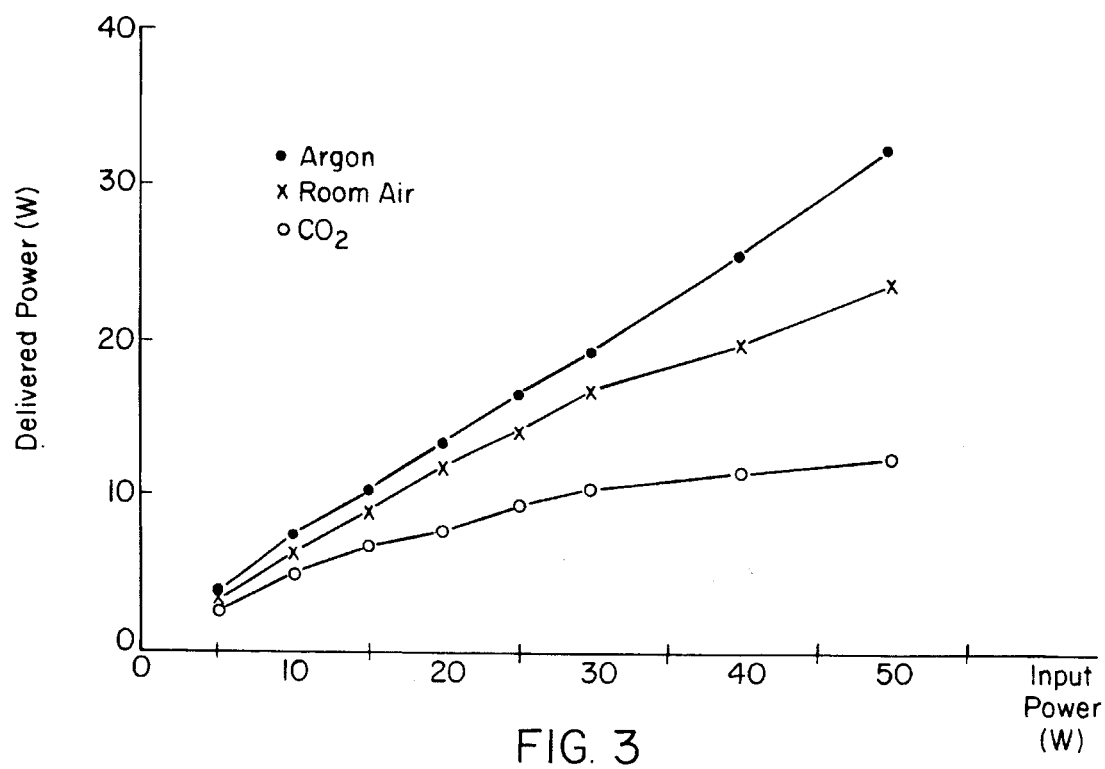
FIG. 3 is an illustration of the power transmission characteristics of a $CO_2$ laser beam in room air, carbon dioxide anti argon.
Figure 4:
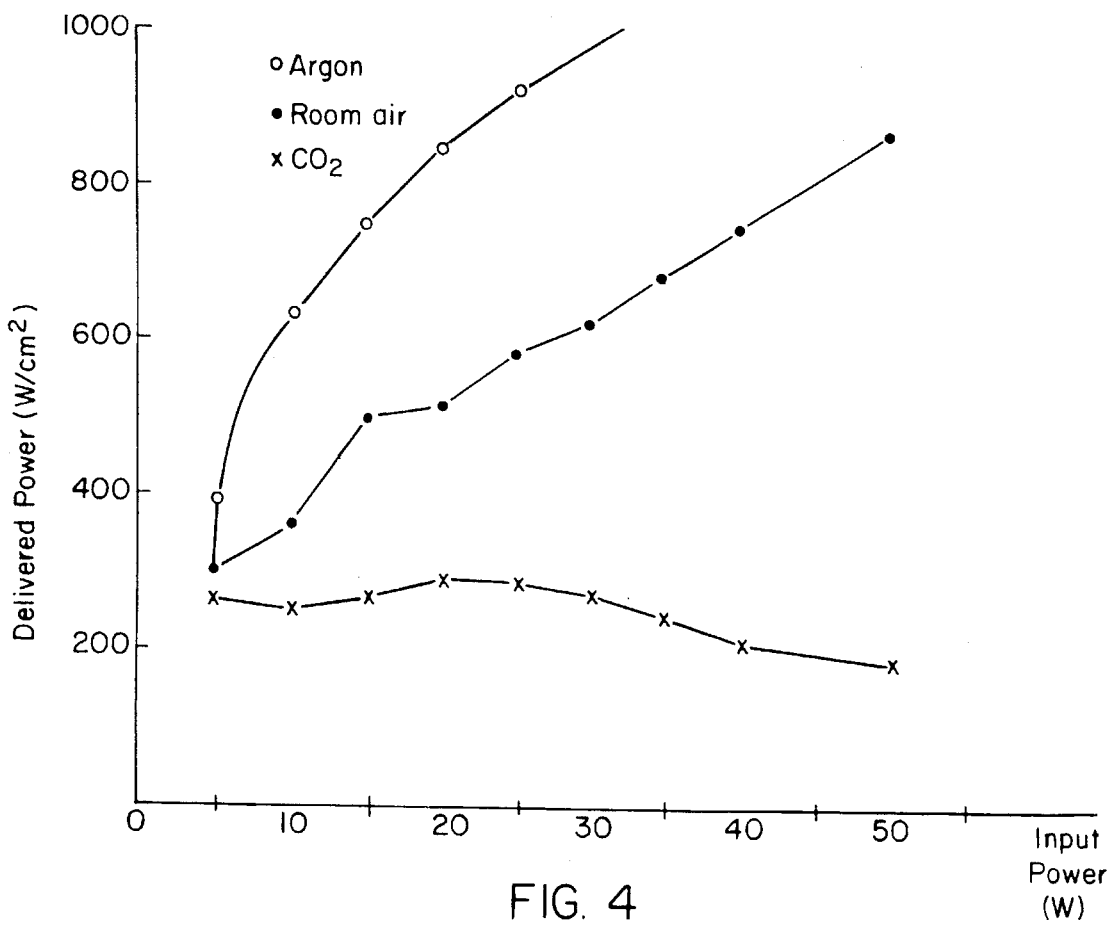
FIG. 4 is an illustration of the power density characteristics of a $CO_2$ laser beam in room air, carbon dioxide and argon.

The improved performance of the laser beam energy at the treatment site using even a small amount of purge gas such as argon can be seen in FIGS. 3 and 4. FIG. 3 depicts the power transmission characteristics for room air, carbon dioxide, and argon, as represented by the legends in FIG. 3, where the ordinate is delivered power in watts and the abscissa is the input power in watts. The power density is portrayed in FIG. 4 for room air, carbon dioxide and argon using the same legends where the ordinate is delivered power in watts per square centimeter and the abscissa is input power in watts.

Figure 2:
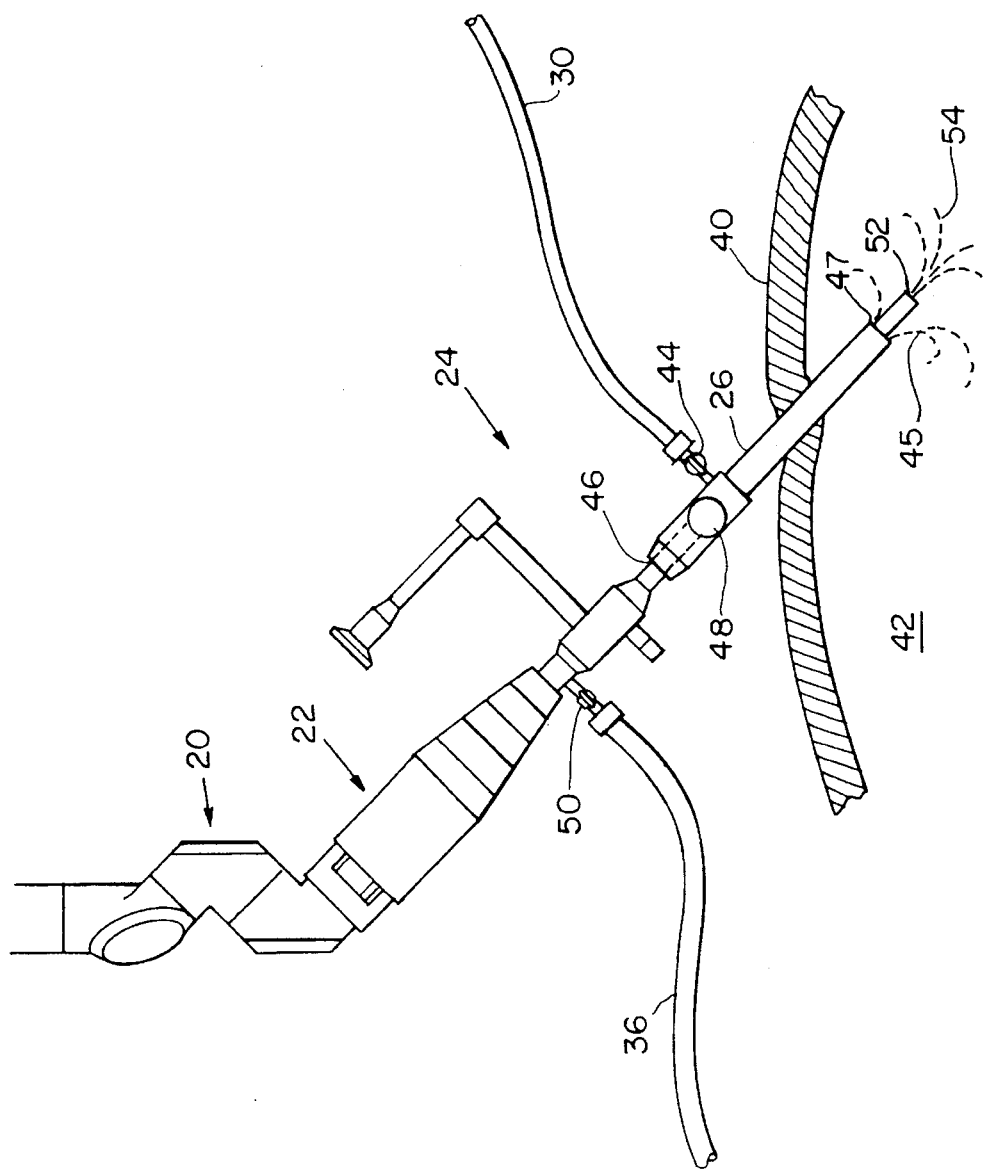
FIG. 2 is an enlarged view of the laparoscope and laser coupler at the distal end of the delivery system in FIG. 1.
Figure 5:
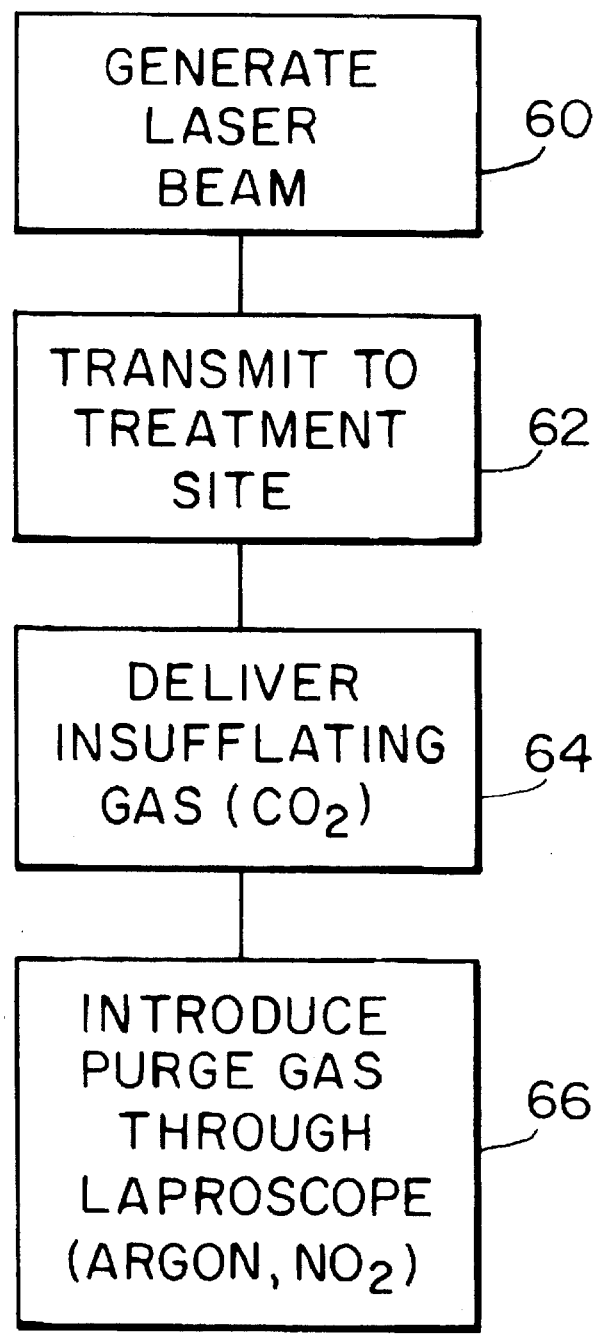
FIG. 5 is a block diagram of the improved medical laser treatment method according to this invention.

The improved medical laser treatment method according to this invention may be employed with the apparatus as shown in FIGS. 1 and 2, or any other suitable equipment. A laser beam is generated, step 60, FIG. 5, such as a 10.6 μ wavelength laser beam generated by a conventional $CO_2$ surgical laser. The beam is transmitted to a treatment site 62 where there is also present an insufflating gas such as carbon dioxide which has been delivered there to expand the body cavity at the treatment site 64. While the surgeon is manipulating the generated laser beam and the insufflating gas is present, purge gas is introduced 66 through the laparoscope operating channel with a small flow that is sufficient to oppose the influx of carbon dioxide or other insufflating gas which would absorb and/or diffuse the laser beam energy being delivered to the treatment site.

Although specific features of this invention are shown in some drawings and not others, this is for convenience only as each feature may be combined with any or all of the other features in accordance with the invention.

Other embodiments will occur to those skilled in the art and are within the following claims:

What is claimed is:

1. An improved medical treatment laser system including a gas laser for generating a beam of laser energy at a predetermined wavelength, means for transmitting the beam of laser energy to a medical treatment site, and means for delivering to the medical treatment site an insufflating gas which use is absorbent at the predetermined wavelength, the improvement comprising:

means for introducing, to the means for delivering the laser beam a non-absorbent purge gas which is transparent to the predetermined wavelength of the gas laser at a flow rate for opposing the influx of insufflating gas to the means for delivering and reducing resonant absorption of the laser beam.

2. The improved medical treatment laser system of claim 1 in which said insufflating gas is $CO_2$.

3. The improved medical treatment laser system of claim 1 in which said gas laser is a $CO_2$ laser.

4. The improved medical treatment laser system of claim 1 in which said purge gas is inert.

5. The improved medical treatment laser system of claim 1 in which said purge gas ms argon.

6. The improved medical treatment laser system of claim 1 in which said means for transmitting includes a laparoscope.

7. The improved medical treatment laser system of claim 1 in which said means for delivering includes a cannula associated with said laparoscope.

8. The improved medical treatment laser system of claim 7 in which said means for introducing includes port means on said laparoscope for receiving said purge gas.

9. The improved medical treatment laser system of claim 1 in which said purge gas is introduced at a flow rate of approximately 0.1 to 0.5 liters per minute.

10. An improved medical laser treatment method comprising:

generating a beam of laser energy at a predetermined wavelength;

transmitting the beam of laser energy along a path to a medical treatment site;

delivering to the medical treatment site an insufflating gas which is absorbent at the predetermined wavelength; and introducing into the path of the beam of laser energy a non-absorbent purge gas which is transparent to the predetermined wavelength of the laser at a flow rate for opposing the influx of insufflating gas to reduce the resonant absorption of the laser beam energy.

11. The improved medical laser treatment method of claim 10 in which said insufflating gas is $CO_2$.

12. The improved medical laser treatment method of claim 10 in which said purge gas is inert.

13. The improved medical laser treatment method of claim 10 in which said purge gas is argon.

14. The improved medical laser treatment method of claim 10 in which said purge gas is introduced at approximately 0.1 to 0.5 liters per minute.

\* \* \* \* \*